United States Patent
Hung et al.

(10) Patent No.: US 10,070,847 B2
(45) Date of Patent: Sep. 11, 2018

(54) OVULATION TESTER

(71) Applicants: Chien-Hsiung Hung, New Taipei (TW); Cherng-Jye Jeng, New Taipei (TW)

(72) Inventors: Chien-Hsiung Hung, New Taipei (TW); Cherng-Jye Jeng, New Taipei (TW)

( * ) Notice: Subject to any disclaimer, the term of this patent is extended or adjusted under 35 U.S.C. 154(b) by 344 days.

(21) Appl. No.: 14/990,844

(22) Filed: Jan. 8, 2016

(65) Prior Publication Data

US 2017/0119357 A1    May 4, 2017

(30) Foreign Application Priority Data

Oct. 29, 2015 (TW) .............................. 104217332 U

(51) Int. Cl.
| | |
|---|---|
| A61B 10/00 | (2006.01) |
| A61B 90/57 | (2016.01) |
| A61B 5/00 | (2006.01) |
| A61B 5/145 | (2006.01) |
| A61B 17/00 | (2006.01) |

(52) U.S. Cl.
CPC ........ *A61B 10/0012* (2013.01); *A61B 5/0077* (2013.01); *A61B 5/14507* (2013.01); *A61B 5/6898* (2013.01); *A61B 10/0051* (2013.01); *A61B 90/57* (2016.02); *A61B 2010/0025* (2013.01); *A61B 2017/00876* (2013.01)

(58) Field of Classification Search
CPC ........ A61B 10/0012; A61B 2010/0025; A61B 5/0082; A61B 5/14507; A61B 10/0051
See application file for complete search history.

(56) References Cited

U.S. PATENT DOCUMENTS

| | | | | |
|---|---|---|---|---|
| 4,815,835 | A * | 3/1989 | Ortueta Corona | ........................... A61B 10/0012 359/379 |
| 5,267,087 | A * | 11/1993 | Weidemann | ....... A61B 10/0012 359/385 |
| 5,572,370 | A * | 11/1996 | Cho | ........................ G02B 25/02 359/379 |
| 6,582,377 | B1 * | 6/2003 | Van Michaels | .... A61B 10/0012 359/379 |
| 2006/0018043 | A1 * | 1/2006 | Gontier | .............. A61B 10/0012 359/804 |
| 2011/0282247 | A1 * | 11/2011 | Denise | ................. A61B 5/0059 600/588 |

FOREIGN PATENT DOCUMENTS

JP          08068790 A  *  3/1996

\* cited by examiner

*Primary Examiner* — Kristen Matter

(57) ABSTRACT

An ovulation tester contains: a first body and a second body. The first body is cylindrical and includes a first connecting portion, a first holding disc, and a switch. The switch has a first coupling section which corresponds to a second coupling section of the first body, between the switch and the first holding disc are defined a power supply assembly and a light-emitting element below the power supply assembly, and between the light-emitting element and the first holding disc is defined a light diffuser. The second body is cylindrical and is connected with the first body, the second body includes a second connecting portion for corresponding to the first connecting portion of the first body, a second holding disc for corresponding to the first connecting portion of the first body, and at least one lens in the inner wall thereof below the second holding disc.

9 Claims, 7 Drawing Sheets

OVULATION TESTER

FIELD OF THE INVENTION

The present invention relates to an ovulation tester which is used repeatedly and easily, and the first body and the second body are connected together fixedly, so the user's saliva does not drop from the first holding disc or the second holding disc.

BACKGROUND OF THE INVENTION

A conventional ovulation test is employed to test peak level of user's luteinizing hormone and its accuracy is only 75%. The ovulation test can predict ovulating time but cannot judge exactly ovulating time. For example, the ovulation test shows positive reaction, yet it does not indicate ovulation period, and user may ovulate within 24 to 72 hours after the ovulation test appears positive reaction. Furthermore, the ovulation test is expensive and cannot be used repeatedly and easily.

The present invention has arisen to mitigate and/or obviate the afore-described disadvantages.

SUMMARY OF THE INVENTION

The primary objective of the present invention is to provide an ovulation tester which is used repeatedly and easily, and the first body and the second body are connected together fixedly, so the user's saliva does not drop from the first holding disc or the second holding disc.

Another objective of the present invention is to provide an ovulation tester which tests the user's saliva and determines safety period, transition period, or ovulatory period precisely.

To obtain the above objectives, an ovulation tester provided by the present invention contains: a first body and a second body.

The first body is cylindrical and includes a first connecting portion arranged on an inner wall thereof, a first holding disc above the first connecting portion, and a switch formed in a top thereof, and the switch has a first coupling section which corresponds to a second coupling section of the first body, between the switch and the first holding disc are defined a power supply assembly and a light-emitting element below the power supply assembly, and between the light-emitting element and the first holding disc is defined a light diffuser.

The second body is cylindrical and being connected with a bottom of the first body, the second body includes a second connecting portion arranged on a top of an outer wall thereof so as to correspond to the first connecting portion of the first body, a second holding disc mounted in a top of an inner wall thereof and corresponding to the first connecting portion of the first body, and at least one lens in the inner wall thereof below the second holding disc.

The first connecting portion of the first body is a magnet magnetically attracting with the second connecting portion which is made of metal material or is another magnet; or the first connecting portion of the first body retains with the second connecting portion of the second body.

The second body also includes a first groove and a second groove which are formed around the outer wall of the second body, and the first groove is located above the second groove, the second body further includes a flexible hook extending outwardly from the second groove.

A clamping assembly is connected with a bottom of the second body.

The clamping assembly includes a first clamp foot, a second clamp foot, and a torsion spring fixed between the first clamp foot and the second clamp foot, wherein the second clamp foot has a through orifice for corresponding to the at least one lens of the second body and has an accommodation seat extending upwardly from the second clamp foot, and the accommodation seat has a peripheral rib for corresponding to the first groove of the second body and has a locking hole for corresponding to the flexible hook of the second body.

The accommodation seat has a fixing protrusion for corresponding to the second holding disc of the second body.

The first clamp foot has a first pad disposed thereon, and the second clamp foot has a second pad mounted thereon.

A camera lens of the cell phone connects with the clamping assembly, and the cell phone has a camera lens which corresponds to the through orifice of the second clamp foot.

DETAILED DESCRIPTION OF THE FIRST EMBODIMENTS

Figure 1:
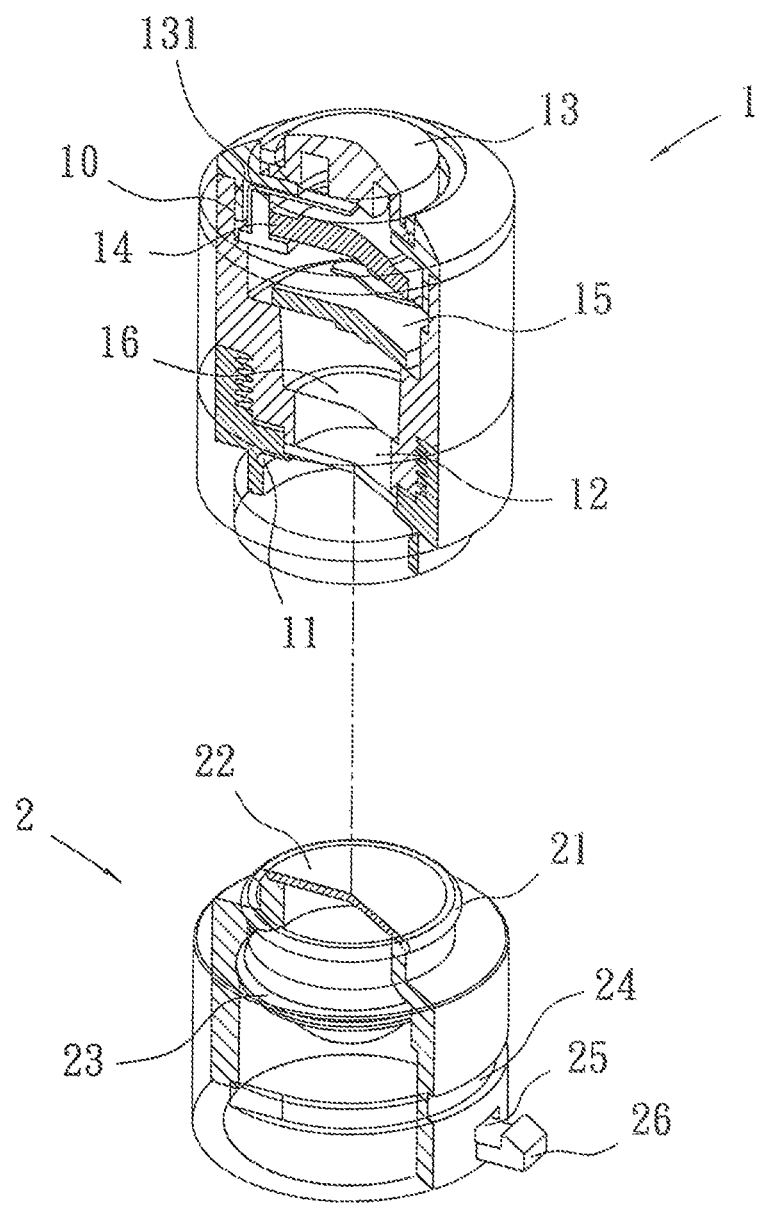
FIG. 1 is a cross-sectional perspective view showing the exploded components of an ovulation tester according to a first embodiment of the present invention.
Figure 2:
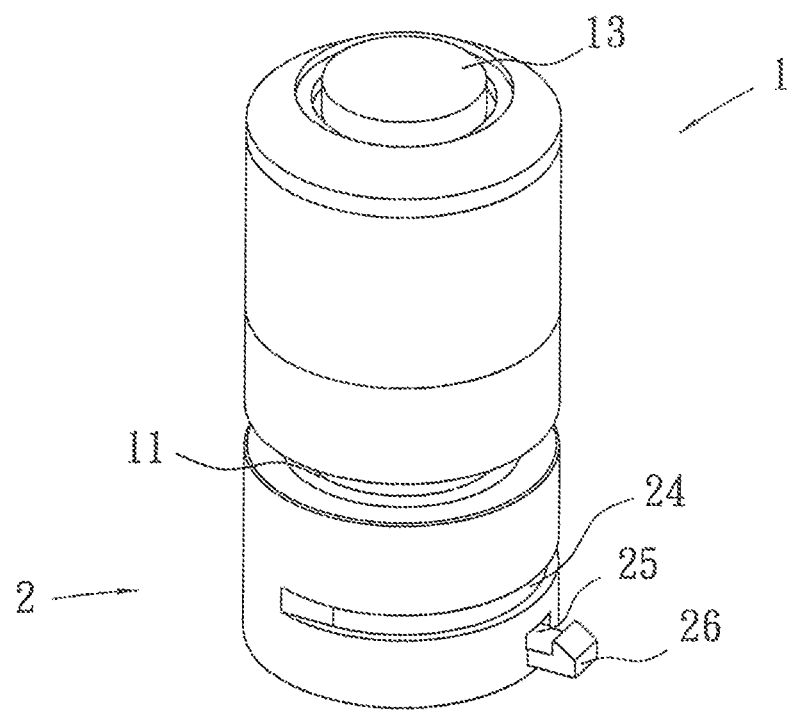
FIG. 2 is a perspective view showing the assembly of the ovulation tester according to the first embodiment of the present invention.
Figure 3:
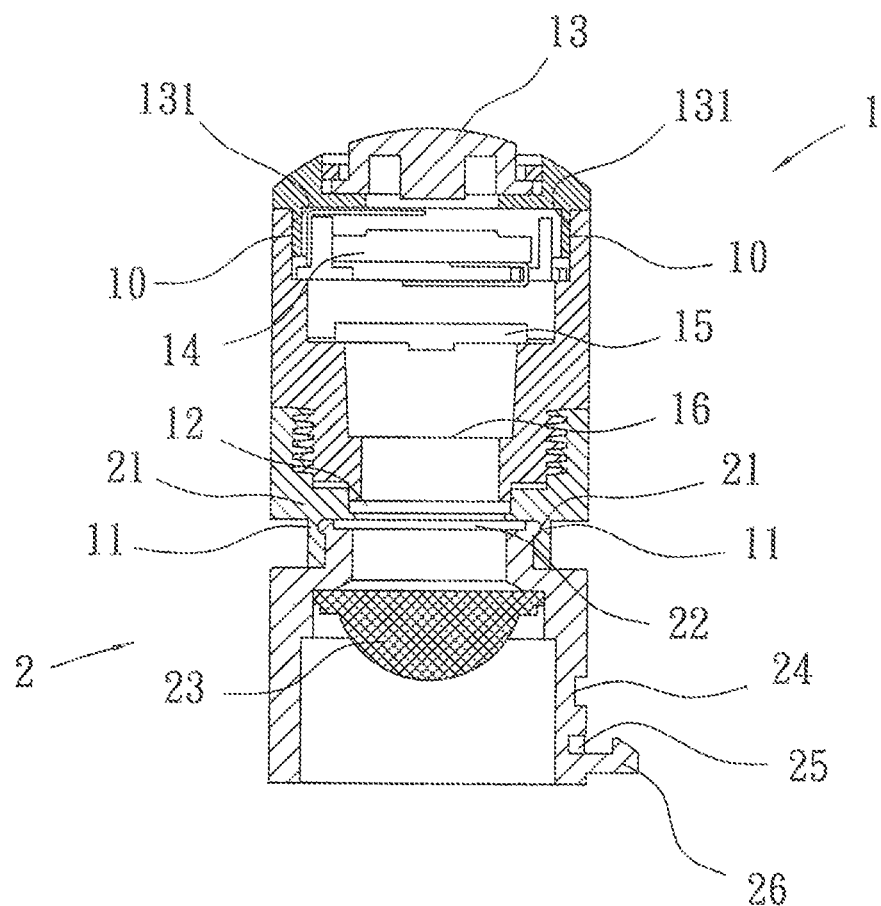
FIG. 3 is a cross sectional view showing the assembly of the ovulation tester according to the first embodiment of the present invention.
Figure 4:
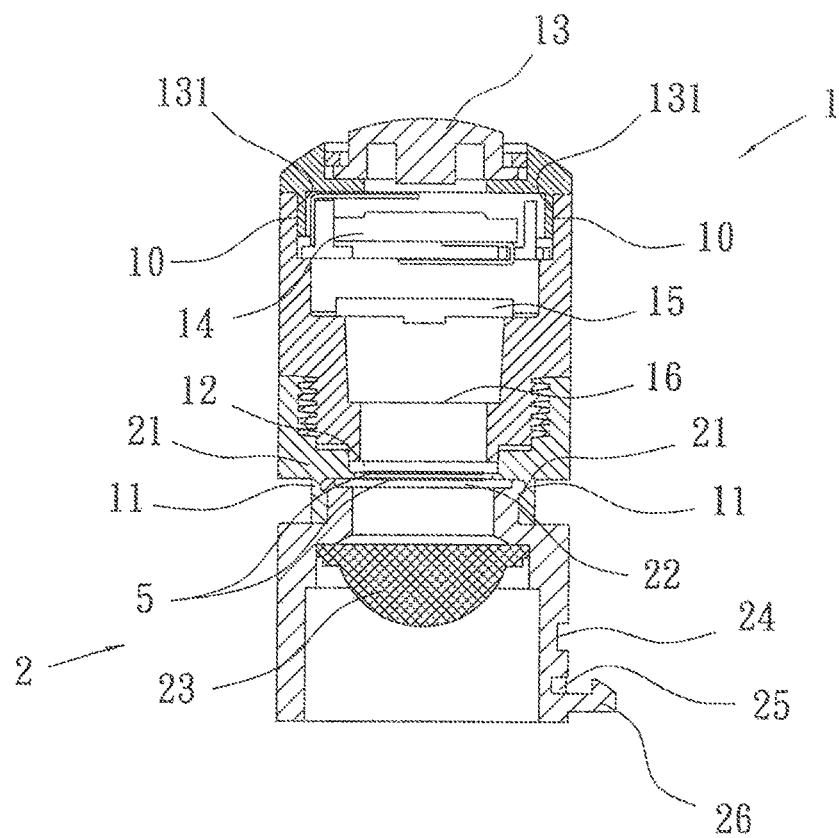
FIG. 4 is a cross sectional view showing the assembly of the ovulation tester according to the first embodiment of the present invention.

FIG. 1 is a cross-sectional perspective view showing the exploded components of an ovulation tester according to a first embodiment of the present invention. FIG. 2 is a perspective view showing the assembly of the ovulation tester according to the first embodiment of the present invention. FIG. 3 is a cross sectional view showing the assembly of the ovulation tester according to the first embodiment of the present invention. FIG. 4 is a cross sectional view showing the operation of the ovulation tester according to the first embodiment of the present invention. With reference to FIGS. 1 to 4, the ovulation tester comprises a first body 1 and a second body 2.

The first body 1 is cylindrical and includes a first connecting portion 11 arranged on an inner wall thereof, a first holding disc 12 above the first connecting portion 11, and a switch 13 formed in a top thereof, wherein the switch 13 has a first coupling section 131 which is threads or a retainer and corresponds to a second coupling section 10 of the first body 1. Between the switch 13 and the first holding disc 12 are defined a power supply assembly 14 and a light-emitting element 15 below the power supply assembly 14, and between the light-emitting element 15 and the first holding disc 12 is defined a light diffuser 16. In this embodiment, the light-emitting element 15 is a light-emitting diode. Thereby, the first coupling section 131 of the switch 13 unscrews from the second coupling section 10 of the first body 1 so as to replace the power supply assembly 14, and the first coupling section 131 of the switch 13 screws with the second coupling section 10 of the first body 1.

The second body 2 is cylindrical and is connected with a bottom of the first body 1, the second body 2 includes a second connecting portion 21 arranged on a top of an outer wall thereof so as to correspond to the first connecting portion 11 of the first body 1, a second holding disc 22 mounted in a top of an inner wall thereof and corresponding to the first connecting portion 11 of the first body 1, and at least one lens 23 in the inner wall thereof below the second holding disc 22. In this embodiment, the first connecting portion 11 of the first body 1 retains with the second connecting portion 21 of the second body 2. Preferably, the first connecting portion 11 of the first body 1 can be a magnet magnetically attract with the second connecting portion 21 which is made of metal material or is another magnet. The second body 2 also includes a first groove 24 and a second groove 25 which are formed around the outer wall of the second body 2, and the first groove 24 is located above the second groove 25. The second body 2 further includes a flexible hook 26 extending outwardly from the second groove 25.

The ovulation tester is operated easily, for example, the first connecting portion 11 of the first body 1 is removed from the second connecting portion 21 of the second body 2 so as to expose the first holding disc 12 and the second holding disc 22, and user's saliva 5 is applied on the first holding disc 12 or the second holding disc 22 and is dry to form crystallization on the first holding disc 12 or the second holding disc 22 after five minutes, the first connecting portion 11 is connected with the second connecting portion 21 so that the first body 1 and the second body 2 couple together. The user's saliva 5 on the first holding disc 12 or the second holding disc 22 is viewed through the light diffuser 16 by way of the light-emitting element 15 and the at least one lens 23, wherein when the crystallization foams slightly, it means the user is in safety period; when the crystallization has lots of bubbles, it represents the user is in transition period; and when the crystallization looks like pine needles or snowflakes, it denotes the user is in ovulatory period. Thereby, the ovulation tester is capable of observing the crystallization by using the light-emitting element 15, the light diffuser 16, and the at least one lens 23 so as to determine the user is in the safety period, the transition period or the ovulatory period. Preferably, estrogen in cervical mucus can be also applied on the first holding disc 12 or the second holding disc 22 so as to observe its crystallization and to determine the user is in the safety period, the transition period or the ovulatory period.

Figure 5:
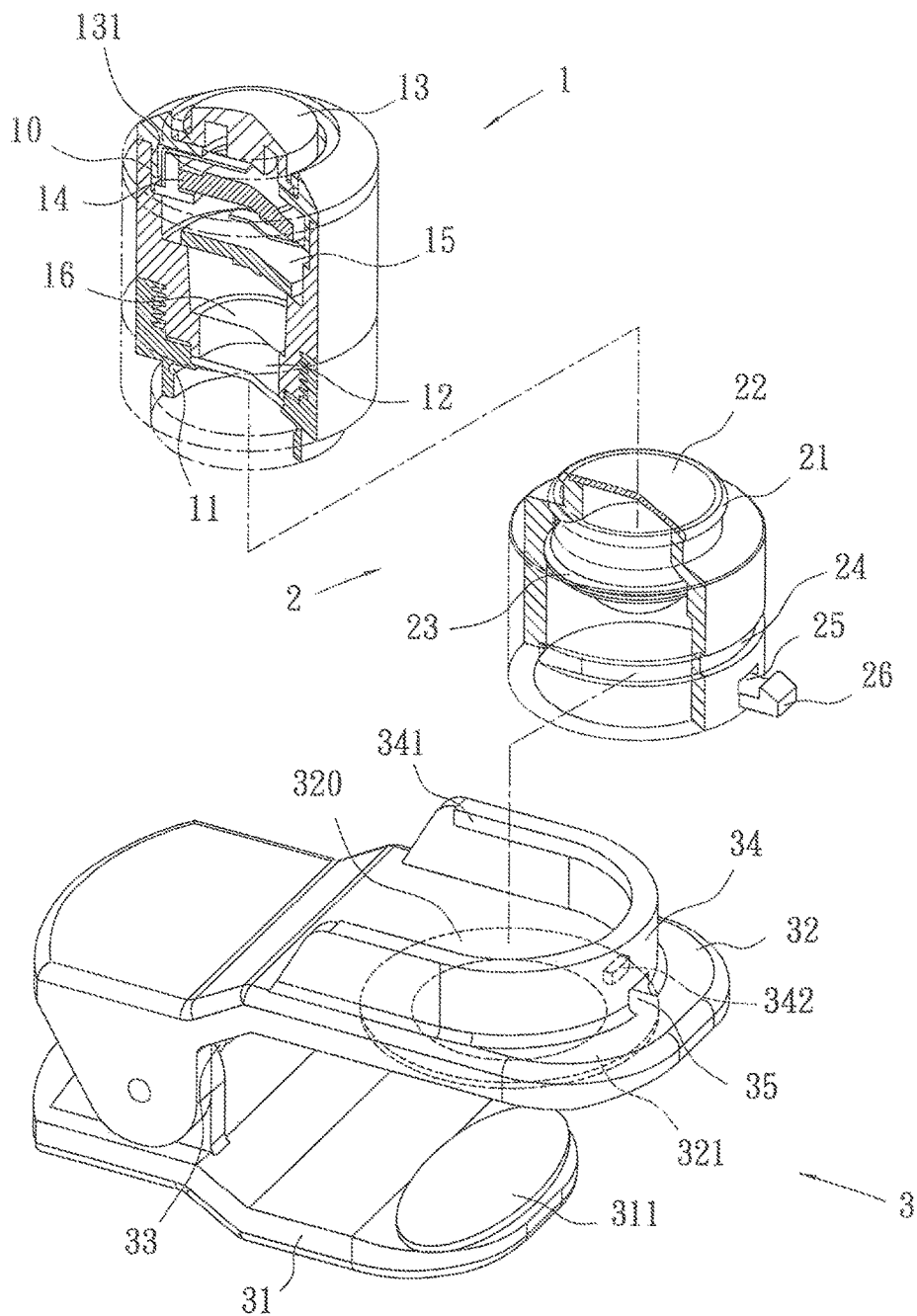
FIG. 5 is a cross-sectional perspective view showing the exploded components of the ovulation tester according to a second embodiment of the present invention.
Figure 6:
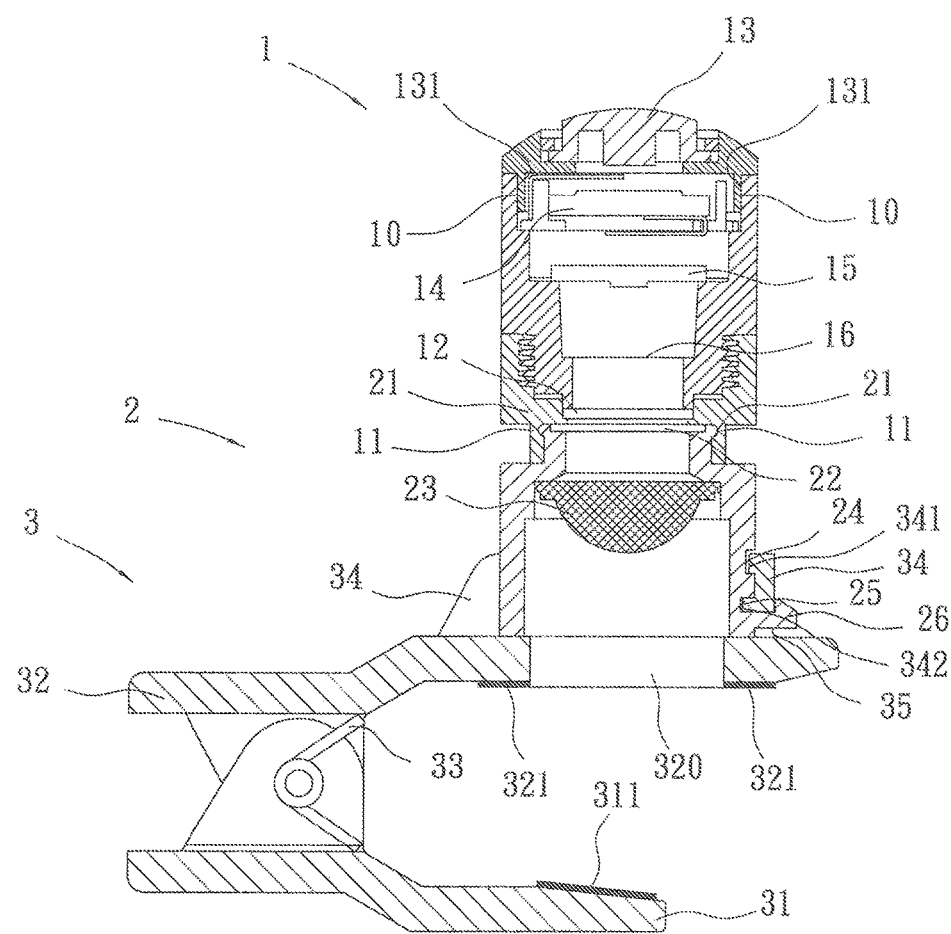
FIG. 6 is a cross sectional view showing the assembly of the ovulation tester according to the second embodiment of the present invention.
Figure 7:
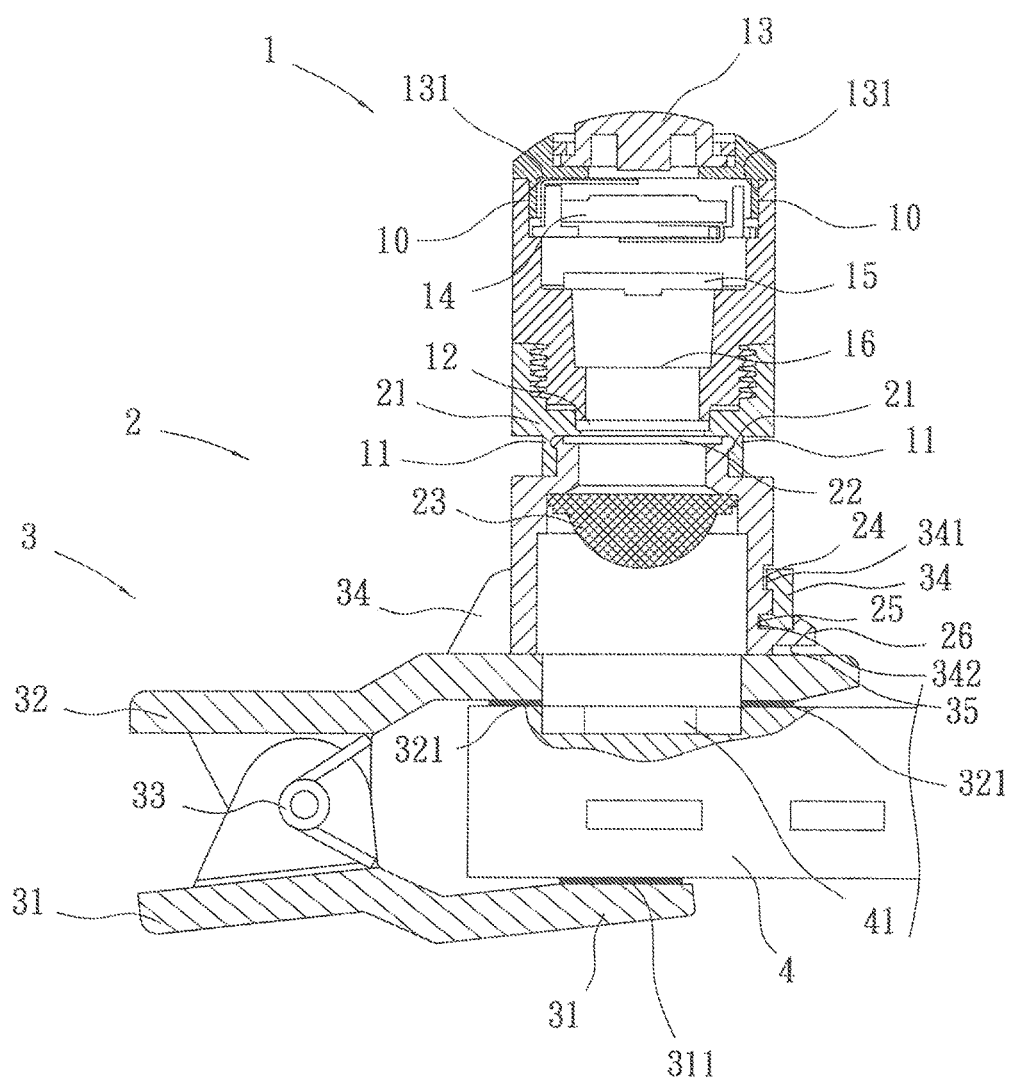
FIG. 7 is a cross sectional view showing the operation of the ovulation tester according to the second embodiment of the present invention.

FIG. 5 is a cross-sectional perspective view showing the exploded components of the ovulation tester according to a second embodiment of the present invention. FIG. 6 is a cross sectional view showing the assembly of the ovulation tester according to the second embodiment of the present invention. FIG. 7 is a cross sectional view showing the operation of the ovulation tester according to the second embodiment of the present invention.

Referring to FIGS. 5 and 6, a difference of the ovulation tester of the second embodiment from that of the first embodiment comprises: a clamping assembly 3 connected with a bottom of the second body 2. The clamping assembly 3 includes a first clamp foot 31, a second clamp foot 32, and a torsion spring 33 fixed between the first clamp foot 31 and the second clamp foot 32. The second clamp foot 32 has a through orifice 302 for corresponding to the at least one lens 23 of the second body 2 and has an accommodation seat 34 extending upwardly from the second clamp foot 32, and the accommodation seat 34 has a peripheral rib 341 for corresponding to the first groove 24 of the second body 2, a locking hole 35 for corresponding to the flexible hook 26 of the second body 2, and a fixing protrusion 342 for corresponding to the second holding disc 22 of the second body 2. To fix a cell phone 4 securely, the first clamp foot 31 has a first pad 311 disposed thereon, and the second clamp foot 32 has a second pad 321 mounted thereon. As connecting the cell phone 4 with the clamping assembly 3, a camera lens 41 of the cell phone 4 corresponds to the through orifice 320 of the second clamp foot 32. In this embodiment, the accommodation seat 34 is formed in U shape. In another embodiment, the accommodation seat 34 is formed in other shapes. As desiring to connect the second body 2 with the clamping assembly 3, the accommodation seat 34 of the clamping assembly 3 is fitted with the first groove 24 of the second body 2, the second holding disc 22 of the second body 2 retains with the fixing protrusion 342, and the flexible hook 26 of the second body 2 engages with the locking hole 35 of the accommodation eat 34. Thereafter, the first clamp foot 31 and the second clamp foot 32 of the clamping assembly 3 clamp the cell phone 4, wherein the camera lens 41 of the cell phone 4 corresponds to the through orifice 320 of the second clamp foot 32 and the at least one lens 23 of the second body 2, and the camera lens 41 automatically focuses the crystallization of the user's saliva 5 on the first holding disc 12 or the second holding disc 22, the light-emitting element 15 illuminates lights to the light diffuser 16, and the light diffuser 16 diffuses the lights onto the first holding disc 12 or the second holding disc 22, hence the cell phone 4 photographs the crystallization of the user's saliva 5 and compares a shape of the crystallization of the user's saliva 5, as illustrated in FIG. 7.

The first connecting portion 11 of the first body 1 is connected with or removed from the second connecting portion 21 of the second body 2 so that the user's saliva 5 is applied on the first holding disc 12 of the first body 1 or the second holding disc 22 of the second body 2. The light diffuser 16 diffuses the lights onto the first holding disc 12 or the second holding disc 22 from the light-emitting element 15. Preferably, the power supply assembly 14 is replaced. In addition, the clamping assembly 3 clamps the cell phone 4, and the camera lens 41 of the cell phone 4 automatically adjusts focal distance and photographs the crystallization of the user's saliva 5 on the first holding disc 12 or the second holding disc 22, thus using the ovulation tester repeatedly and easily. Preferably, the first body 1 and the second body 2 are connected together fixedly, and the user's saliva 5 does not drop from the first holding disc 12 or the second holding disc 22.

While the first embodiments of the invention have been set forth for the purpose of disclosure, modifications of the disclosed embodiments of the invention as well as other embodiments thereof may occur to those skilled in the art. The scope of the claims should not be limited by the first embodiments set forth in the examples, but should be given the broadest interpretation consistent with the description as a whole.

What is claimed is:

1. An ovulation tester comprising:
a first cylindrical body comprising:
a first connecting portion arranged on an inner wall of the first cylindrical body;
a first holding disc above the first connecting portion;
a switch formed in a top of the first cylindrical body, and the switch including a first coupling section coupled to a second coupling section;
a power supply assembly located between the switch and the first holding disc;
a light-emitting element below the power supply assembly; and
a light diffuser between the light-emitting element and the first holding disc; and
a second cylindrical body connected with a bottom of the first cylindrical body, the second cylindrical body comprising:
a second connecting portion arranged on a top of an outer wall of the second cylindrical body, the second connecting portion configured to connect to the first connecting portion of the first cylindrical body;
a second holding disc mounted in a top of an inner wall of the second cylindrical body; and
at least one lens within the inner wall of the second cylindrical body below the second holding disc.

2. The ovulation tester as claimed in claim 1, wherein the first connecting portion of the first cylindrical body is a magnet magnetically attracted to the second connecting portion, and the second connecting portion is made of metal material or is another magnet.

3. The ovulation tester as claimed in claim 1, wherein the second cylindrical body further comprises a first groove and a second groove, the first and second grooves are formed around the outer wall of the second cylindrical body, the first groove is located above the second groove, and the second cylindrical body further includes a flexible hook extending outwardly from the second groove.

4. The ovulation tester as claimed in claim 3, wherein a clamping assembly is connected with a bottom of the second cylindrical body.

5. The ovulation tester as claimed in claim 4, wherein the clamping assembly includes a first clamp foot, a second clamp foot, and a torsion spring fixed between the first clamp foot and the second clamp foot; wherein the second clamp foot has a through orifice corresponding to the at least one lens of the second cylindrical body and an accommodation seat extending upwardly from the second clamp foot, the accommodation seat having a peripheral rib corresponding to the first groove of the cylindrical second body and a locking hole corresponding to the flexible hook of the second cylindrical body.

6. The ovulation tester as claimed in claim 5, wherein the accommodation seat has a fixing protrusion corresponding to the second holding disc of the second cylindrical body.

7. The ovulation tester as claimed in claim 5, wherein the first clamp has a first pad disposed thereon, and the second foot has a second pad mounted thereon.

8. The ovulation tester as claimed in claim 7, wherein a camera lens of a cell phone connects with the clamping assembly, and the camera lens corresponds to the through orifice of the second clamp foot.

9. The ovulation tester as claimed in claim 1, wherein a clamping assembly is connected with a bottom of the second cylindrical body.

* * * * *